(12) United States Patent
Sircom et al.

(10) Patent No.: US 7,513,888 B2
(45) Date of Patent: Apr. 7, 2009

(54) NEEDLE GUARDS

(75) Inventors: Richard C. Sircom, Dartmouth (CA); David J. French, Gatineau (CA)

(73) Assignee: Smiths Medical ASD, Inc., Rockland, MA (US)

( * ) Notice: Subject to any disclaimer, the term of this patent is extended or adjusted under 35 U.S.C. 154(b) by 274 days.

(21) Appl. No.: 10/905,884

(22) Filed: Jan. 25, 2005

(65) Prior Publication Data

US 2005/0182362 A1    Aug. 18, 2005

Related U.S. Application Data

(60) Provisional application No. 60/544,352, filed on Feb. 17, 2004.

(51) Int. Cl.
*A61M 5/00* (2006.01)
(52) U.S. Cl. .................. 604/110; 604/192; 604/198
(58) Field of Classification Search ................ 604/110, 604/154, 263, 164, 165, 192–198, 181, 187, 604/111, 117
See application file for complete search history.

(56) References Cited

U.S. PATENT DOCUMENTS

| | | |
|---|---|---|
| 4,850,994 A | 7/1989 | Zerbst et al. |
| 4,929,241 A | 5/1990 | Kulli |
| 5,015,242 A | 5/1991 | Heifetz |
| 5,026,356 A | 6/1991 | Smith |
| 5,053,017 A | 10/1991 | Chamuel |
| 5,135,504 A | 8/1992 | McLees |
| 5,215,528 A | 6/1993 | Purdy et al. |
| 5,300,045 A | 4/1994 | Plassche |
| 5,322,517 A | 6/1994 | Sircom et al. |
| 5,328,482 A | 7/1994 | Sircom et al. |
| 5,344,408 A | 9/1994 | Partika |
| 5,348,544 A | 9/1994 | Sweeney et al. |
| 5,395,347 A | 3/1995 | Blecher et al. |
| 5,409,461 A | 4/1995 | Steinman |
| 5,423,766 A | 6/1995 | Di Cesare |
| 5,425,720 A | 6/1995 | Rogalsky et al. |
| 5,458,658 A | 10/1995 | Sircom |

(Continued)

FOREIGN PATENT DOCUMENTS

JP    2002-102345    9/2002

(Continued)

OTHER PUBLICATIONS

PCT *International Search Report*, mailed May 25, 2005.

(Continued)

*Primary Examiner*—Kevin C. Sirmons
*Assistant Examiner*—Phillip Gray
(74) *Attorney, Agent, or Firm*—Wood, Herron & Evans, LLP

(57) ABSTRACT

A needle guard (1) based upon a canting plate (6) becomes lockingly engaged with the needle (2) shaft both upon retraction of the needle tip within the guard (1), and upon any attempt to cause the needle tip to reemerge from the guard (1). The plate (6) is positioned to rotate into locking engagement with the shaft of the needle (2) both when an attempt is made to further withdraw the needle from the needle guard (1) and when an attempt is made to cause the needle tip to reemerge from the needle guard (1).

13 Claims, 2 Drawing Sheets

U.S. PATENT DOCUMENTS

| | | | |
|---|---|---|---|
| 5,466,223 A | 11/1995 | Bressler et al. | |
| 5,496,274 A | 3/1996 | Graves et al. | |
| 5,533,974 A | 7/1996 | Gaba | |
| 5,549,570 A | 8/1996 | Rogalsky | |
| 5,558,651 A | 9/1996 | Crawford et al. | |
| 5,584,809 A | 12/1996 | Gaba | |
| 5,584,810 A | 12/1996 | Brimhall | |
| 5,601,532 A | 2/1997 | Gaba | |
| 5,601,536 A | 2/1997 | Crawford et al. | |
| 5,611,781 A | 3/1997 | Sircom et al. | |
| 5,662,610 A | 9/1997 | Sircom | |
| 5,695,474 A | 12/1997 | Daugherty | |
| 5,697,907 A * | 12/1997 | Gaba | 604/110 |
| 5,735,827 A | 4/1998 | Adwers et al. | |
| 5,879,337 A | 3/1999 | Kuracina et al. | |
| 5,882,337 A | 3/1999 | Bogert et al. | |
| RE36,885 E | 9/2000 | Blecher et al. | |
| 6,117,108 A * | 9/2000 | Woehr et al. | 604/110 |
| 6,203,527 B1 | 3/2001 | Zadini et al. | |
| 6,210,373 B1 | 4/2001 | Allmon | |
| 6,322,537 B1 | 11/2001 | Chang | |
| 6,406,459 B1 | 6/2002 | Allmon | |
| 6,443,929 B1 | 9/2002 | Kuracina et al. | |
| 6,485,468 B2 | 11/2002 | Vojtasek | |
| 6,537,259 B1 | 3/2003 | Niermann | |
| 6,585,704 B2 | 7/2003 | Luther et al. | |
| 6,595,955 B2 * | 7/2003 | Ferguson et al. | 604/110 |
| 6,616,630 B1 | 9/2003 | Woehr et al. | |
| 6,623,458 B2 | 9/2003 | Woehr et al. | |
| 6,629,959 B2 | 10/2003 | Kuracina et al. | |
| 6,652,486 B2 | 11/2003 | Bialecki et al. | |
| 6,652,490 B2 | 11/2003 | Howell | |
| 6,761,706 B2 | 7/2004 | Vaillancourt | |
| 6,796,962 B2 | 9/2004 | Ferguson et al. | |
| 6,832,992 B2 | 12/2004 | Wilkinson | |
| 6,920,546 B2 | 7/2005 | Gochman et al. | |
| 2001/0018573 A1 | 8/2001 | Woehr | |
| 2001/0027298 A1 | 10/2001 | Vojtasek | |
| 2002/0004650 A1 | 1/2002 | Kuracina et al. | |
| 2002/0099339 A1 | 7/2002 | Niermann | |
| 2002/0165498 A1 | 11/2002 | Ward, Jr. | |
| 2002/0169418 A1 | 11/2002 | Menzi et al. | |
| 2002/0177818 A1 | 11/2002 | Vaillancourt | |
| 2002/0193745 A1 | 12/2002 | Ferguson | |
| 2003/0036731 A1 | 2/2003 | Wilkinson et al. | |
| 2003/0100868 A1 | 5/2003 | Ferguson et al. | |
| 2003/0181871 A1 | 9/2003 | Wilkinson et al. | |
| 2003/0199827 A1 | 10/2003 | Thorne | |
| 2004/0049155 A1 | 3/2004 | Schramm | |
| 2004/0078003 A1 | 4/2004 | Smith et al. | |
| 2004/0236288 A1 | 11/2004 | Howell et al. | |
| 2005/0096592 A1 | 5/2005 | Carlyon et al. | |

FOREIGN PATENT DOCUMENTS

| | | |
|---|---|---|
| WO | WO 90/08564 | 9/1990 |

OTHER PUBLICATIONS

PCT *Written Opinion* of the International Searching Authority, mailed May 25, 2005.

* cited by examiner

NEEDLE GUARDS

CROSS-REFERENCE TO RELATED APPLICATION

This application claims the benefit of U.S. Provisional Application No. 60/544,352, filed Feb. 17, 2004, the disclosure of which is incorporated by reference herein.

FIELD OF THE INVENTION

This invention relates to the field of medical devices. In particular, it relates to providing protection for "sharps" such as needles and wires that have been used on a subject and require provision to prevent personnel from receiving a puncture wound from the used device that may give rise to a risk of infection for such personnel. As such, the invention may be characterized as a "needle guard" although it is intended to apply equally to any sharp device akin to a needle or wire that requires protection.

BACKGROUND OF THE INVENTION

U.S. Pat. No. 6,280,419 describes a needle guard device that automatically engages with a needle when the tip of the needle is withdrawn into an enclosing volume or cavity contained within the protective device. The mechanism within the needle guard for engaging with the needle operates on the principle of a canting plate that has a hole through which the shaft of the needle passes. Before deployment of the guard, the plate carrying the hole is oriented perpendicularly to the axis of the needle shaft, and a tight sliding fit exists between the needle shaft and the perimeter of the hole. Once the tip of the needle has been withdrawn into the guard, the plate is caused by a spring to "cant" or rotate from its perpendicular orientation with respect to the needle shaft. By reason of the tight sliding fit between the shaft and the hole in the canting plate, the edge of the perimeter of the hole forcefully engages with the surface of the needle, preventing further retraction of the needle in the direction that would cause the canting plate to cant at an even further angle.

In the design of the needle guard of U.S. Pat. No. 6,280,419, the canting plate acts to arrest the needle shaft against further withdrawal of the needle shaft through the needle guard's cavity. The canting action described above occurs when the needle tip has been withdrawn into the cavity and a sensing arm connected to the canting plate is able to shift its position due to the retraction of the needle tip past an opening in a limb of the sensing arm through which the needle passes prior to the initiation of locking action.

In the specific design of the referenced patent, provision is made for a wire to be present, passing through the core of the needle and the body of the needle guard. As the needle guard and needle are retracted, they slide along this wire. To permit such movement to continue after the needle tip has entered within the cavity of the needle guard, the opening in the limb on the sensing arm is in the form of a slot. The bottom of the slot is large enough to permit passage of the needle shaft before the needle guard is deployed. The slot above the bottom is of a reduced width, sufficient to allow passage of the wire, but narrow enough to prevent the reemergence of the needle tip from the needle guard, once the needle tip has withdrawn from the hole in the limb of the sensing arm. The reemergence of the needle is prevented in this design by the presence of the sides of the limb on the sensing arm that define the borders of the slot. These sides remain in the path that the needle tip would have to follow if it were to attempt to reemerge from the needle guard.

This system for preventing reemergence of the needle tip from the needle guard depends critically upon the engagement of the sidewall of the needle with the sides of the slot in the locking limb on the sensing plate. As the needle wall is of a relatively small thickness, this method for preventing reemergence of the needle tip does not provide maximum reliability.

The present invention provides a system for preventing reemergence of the needle tip which is an alternative to, and may be more reliable than, the system described above.

The invention in its general form will first be described, and then its implementation in terms of specific embodiments will be detailed with reference to the drawings following hereafter. These embodiments are intended to demonstrate the principle of the invention, and the manner of its implementation. The invention in its broadest and more specific forms will then be further described, and defined, in each of the individual claims which conclude this Specification.

SUMMARY OF THE INVENTION

The invention in one aspect is directed to a needle guard having a containment case through which a needle projects. Within a cavity within the case, there is a canting plate having an aperture such as a hole, through which the needle projects, such hole having an inner face surface bounded by first and second circumferential edges that provide a close sliding fit around the needle. An alignment means in the form of a sensing arm coupled to the canting plate is provided to align the circumferential edges for sliding engagement with the needle while the needle tip protrudes from the containment casing. Resilient biasing means act between the casing and the sensing arm to cause the canting plate to rotate with respect to the needle upon withdrawal of the needle tip into the containment cavity. This rotation occurs once the needle tip has been withdrawn past a sensing limb on the sensing arm that may, optionally, contain a slot, hole, or other opening. The canting of the canting plate causes the first and second circumferential edges bounding at the hole in the canting plate to be directed into locking engagement with the surface of the needle shaft.

The canting plate is aligned within the cavity for connection between first and second pressure points connected to the canting plate and first and second abutment means present and carried within the cavity of the containment case. The first pressure point is positioned to engage with the first abutment means upon withdrawal of the needle tip into the needle guard cavity, such engagement effecting the canting of the canting plate to resist further withdrawal of the needle once the tip is within the needle guard. The second pressure point is positioned to engage with the second abutment means once the canting plate has assumed a canted orientation whereby, upon any attempt to cause reemergence of the needle tip from the needle guard, contact between the second pressure point and second abutment means tends to rotate the canting plate so as to further engage the circumferential edges with the surface of the needle shaft.

Thus attempted advancement of the needle in either direction with respect to the containment case, once the canting plate is canted with respect to the needle, causes pressure to be applied through either of the pressure points by the abutment means to effect further locking engagement of the circumferential edges with the surface of the needle. The result is to lockingly contain the needle tip within the containment case against either further withdrawal of the needle or reemergence of the needle.

The sensing arm serves as an alignment means for the canting plate to which it is connected. These parts rotate in unison. Extending from the canting plate, the sensing arm contains a limb which, through a hole, slot or finger, bears against the side of the needle or needle shaft while the needle tip protrudes from the containment casing. So long as the limb on the sensing arm bears against the needle shaft, the canting plate cannot rotate with respect to the needle. Upon retraction of the needle tip past this limb of the sensing arm, the limb, the sensing arm and the connected canting plate are free to rotate, allowing the canting plate to take up a canting orientation that permits locking engagement of the needle guard with the needle.

The limb on the sensing arm may be in the form of an extension to the sensing arm that includes a plate with a hole or slot positioned and dimensioned to receive the needle therethrough before the needle is withdrawn into the needle guard. Or it may simply comprise a finger that prevents displacement of the limb and sensing arm so long as the finger bears against the needle shaft.

As a supplemental protection against reemergence of the needle from the needle guard case, a barrier portion of the limb may be extended below the hole or slot formed therein, such barrier portion resting in the path of the needle when the canting plate has assumed a locking orientation.

By further variation of the invention, an alternate supplemental reemergence barrier may be carried on a separate biased supporting member with a sensing surface. This separate supporting member is carried by the containment case, preferably on the opposite side of the needle to the sensing arm of the locking plate. When the needle tip is drawn past a separate barrier sensing surface, the biased supporting member urges the reemergence barrier into the path of the needle, thereby preventing reemergence of the needle.

The needle guard according to the invention may be employed with or without the presence of a wire passing through the core of the needle. Thus the needle guard of the invention is suited for incorporation with the designs of U.S. Pat. Nos. 5,458,658; 5,611,781 and 5,662,610 to Sircom, as well as with other designs that rely upon the effect of a canting plate.

The foregoing summarizes the principal features of the invention and some of its optional aspects. The invention may be further understood by the description of the preferred embodiments, in conjunction with the drawings, which now follow.

BRIEF DESCRIPTION OF THE DRAWINGS

The accompanying drawings, which are incorporated in and constitute a part of this specification, illustrate embodiments of the invention and, together with the general description of the invention given above and the detailed description of the embodiments given below, serve to explain the principles of the present invention.

DETAILED DESCRIPTION OF THE DRAWINGS

Figure 1:
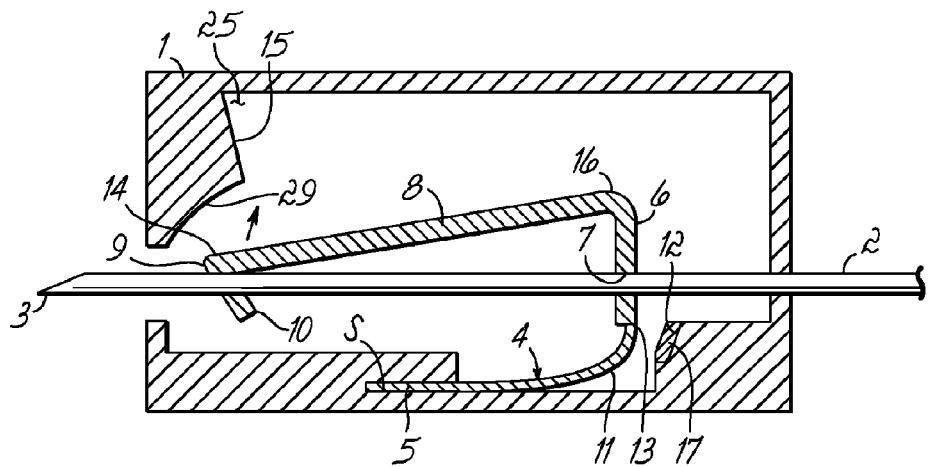
FIG. 1 is a cross-sectional side view of one embodiment of the invention having a containment case containing a locking mechanism of the invention in an armed condition.

In FIG. 1, a containment case 1, which may cylindrically surround a needle 2 with a tip 3, has seated therein a strip of spring metal 4 which serves to provide the locking mechanism of the invention. The base end 5 of the strip of metal 4 is seated in a slot S in the inner wall of the containment case 1 with a close, sliding fit to allow for slight displacement of base end 5. A locking plate portion 6 of the strip 4 has an aperture 7 such as a hole through which needle 2 projects. Strip 4 and plate 6 may be a single piece of metal strip. Alternatively, locking plate portion 6 may be in the form of a hardened steel plate that is spot-welded to thinner spring-shield strip 4. Hole 7 is dimensioned to provide a close sliding fit with needle 2 when the device is in the armed condition shown in FIG. 1. The strip 4 extends with a sensing arm segment or sensing arm 8 with a sensing end 9. The sensing arm 8 may be stiffened by a flange, as by being of "L" shape in cross-section.

Extending from the sensing end 9 is a sensing means 10 which hooks under the needle 2. The sensing means 10 may be the lower portion of a plate which extends downwardly from the sensing end 9, such plate having a hole or slot cut into it (seen in FIG. 2), or may simply be a finger which extends under the needle 2.

A curved portion 11 of the strip 4 is spring-loaded, biasing the locking plate portion 6 to seek to rotate in a clockwise direction in the configuration as shown in FIG. 1. Curved portion 11 of strip 4 biases locking plate portion 6 for rotation, and so portion 11 can be made of thinner spring or other like metal with plate portion 6 being of thicker and harder material.

Figure 2:
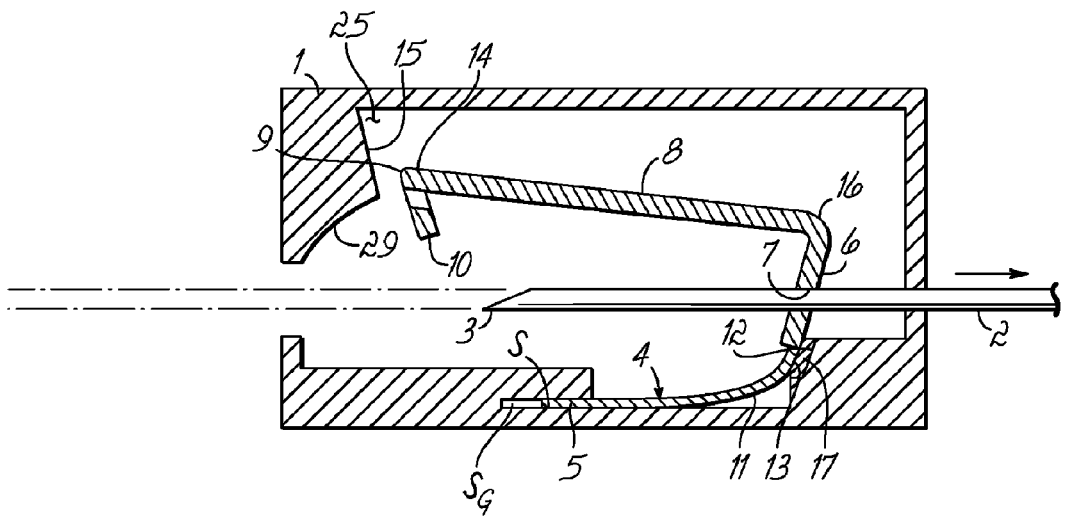
FIGS. 2 and 3 are views similar to FIG. 1 showing the needle withdrawn into the containment case and the locking mechanism engaged with the needle, positioned to prevent further withdrawal of the needle tip from the containment case or reemergence of the needle tip, respectively.

When the needle tip 3 is withdrawn to the right into the containment case 1 past the sensing means 10 as shown in FIG. 2, the sensing means 10 is released to rotate clockwise and upwardly under the urging of the curved, spring-loaded portion 11. The sensing arm 8 also rises upwardly, rotating in the clockwise direction as well. Adjacent inner wall 29 of case 1 may be shaped to conform to the path of travel of end 9 as sensing arm 8 swings upwardly. That upward swinging motion, in turn, urges the locking plate 6 to rotate in a clockwise direction. Because of the close sliding fit between the needle 2 and hole 7, rotation of the locking plate 6 is almost immediately arrested. Also, base end 5 may displace within slot 6 leaving a small gap $S_G$ as seen in FIG. 2 as strip 4 is carried with needle 2.

A first buttressing surface 12 on the inner surface of the case 1 receives the lower end 13 of the locking plate portion 6 of the strip 4. Further attempts to withdraw the needle 2 from the case 1 (to the right in FIG. 3) urge the locking plate 6 to rotate further in the clockwise direction. Due to the adjacent edges of the hole 7 engaging with the surface of the needle 2, substantial actual rotation does not take place, but the locking plate 6 locks firmly into place on the surface of the needle 2, thus preventing further withdrawal of needle 2 from case 1.

Figure 3:
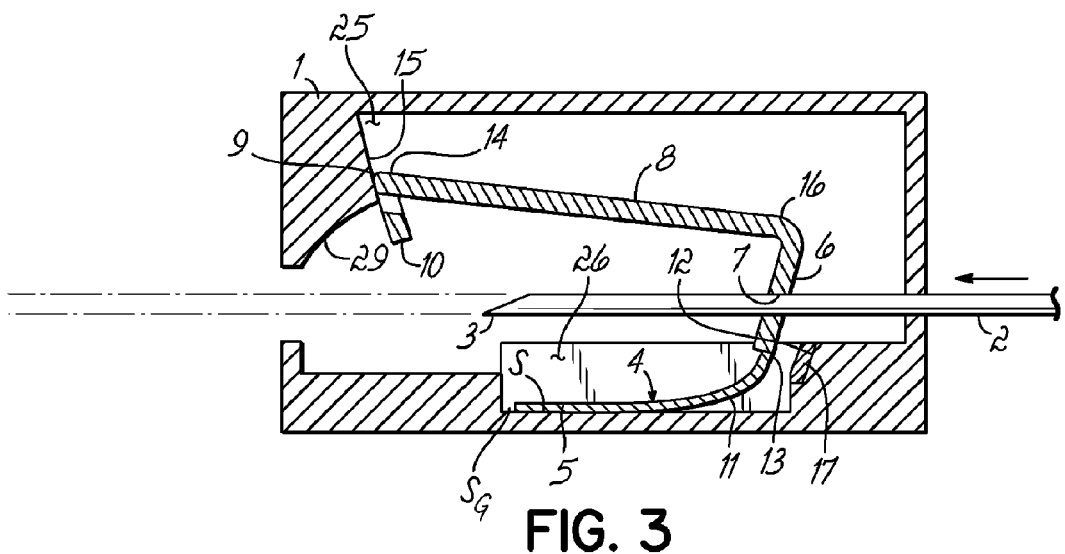

When an attempt is made to advance the needle 2 for reemergence from the case 1, which would be to the left as shown in FIG. 3, the now upwardly rotated sensing arm 8 is carried forward within the case 1 until the upper portion 14 and end 9 of the sensing arm 8 abut against a second abutment 15 on the interior of the case 1. Simultaneously, the base end 5 of the strip 4 may shift forward into gap $S_G$. Any further attempt at advancement of the needle 2 to the left for reemergence from the case 1 applies a force to the upper end 16 of the locking plate 6. As previously, this urges the locking plate 6 to rotate, to thereby effect a further locking engagement with the needle 2. Second abutment 15 is advantageously defined within notch or recess 25 and may present a receding face to end 9. Also, slot S may alternatively open upwardly into case 1 as depicted, for sake of convenience, in only FIG. 3, with the sidewalls 26 (only one shown) of slot S providing confinement to orient strip 4 to ensure that end 9 is aligned with abutment surface 15.

When the upper portion 14 of the sensing arm 8 first rises to its rotated orientation as shown in FIG. 2, it becomes aligned with second abutment 15. Notch or recess 25 may be in the form of a circumferential groove following the curvature of the confinement case 1 thereat to facilitate the desired alignment. Additionally, the first abutment 12 may carry a resilient member 17, such as a resilient pad or coiled spring (the latter not shown), that serves to assist in shifting the base end 5 forwardly in its slot and to maintain a rotational bias of locking plate 6 towards engagement with needle 2.

The motion depicted in FIG. 3 whereby the upper portion 14 and end 9 of the sensing arm 8 has shifted into abutting contact against the second abutment 15 is minimal. The resilient member 17 at the location of the first abutment 12 helps ensure that the lower end of the locking plate 13 is carried forwardly during this slight advancement of the needle, retaining the locking plate 6 in its locking orientation. This further ensures that the locking plate 6 is urged to rotate to effect the further locking engagement with the needle 2. Where member 17 is a resilient pad, the pad may be comprised of resilient polymeric material.

Figure 4:
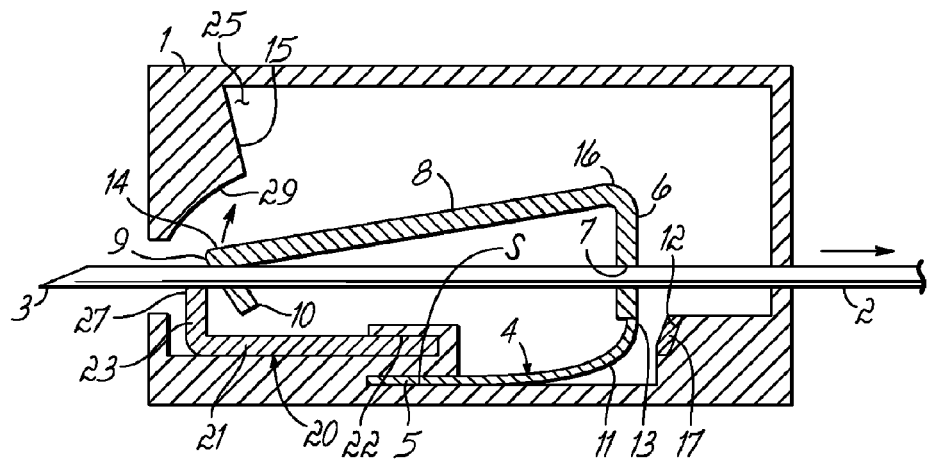
FIG. 4 is a cross-sectional side view of a second embodiment of the invention having a containment case containing a locking mechanism and additional reemergence barrier mounted within the case in an armed configuration.
Figure 5:
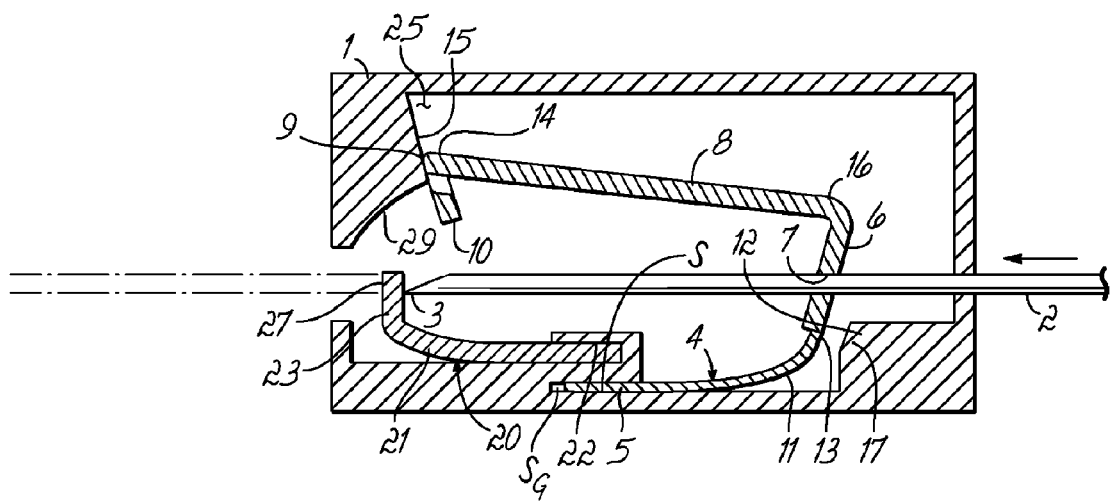
FIG. 5 is a view similar to FIG. 4 with the needle withdrawn into the containment case and the locking mechanism engaged with the needle.

While the needle guard as described in FIGS. 1 to 3 is locked in place against movement of the needle 2, to prevent further withdrawal or reemergence of the needle tip 3 from the case 1, a supplemental reemergence barrier 20 may be provided as seen in FIGS. 4 and 5. This barrier is provided by a second spring-biased strip 21 seated at its base end in a slot 22 within the inner surface of the case 1. At the other end of this second strip 21, a barrier plate 23 is provided with a sensing end 27.

In FIG. 4, the sensing end 27 bears against the side of the needle 2. In FIG. 5 the needle tip 3 has been withdrawn past the sensing end 27, whereupon the spring bias within the strip 21 causes the reemergence barrier plate 23 to rise into the path of the needle 2. Any attempt to advance the needle thereafter for reemergence will be arrested by the reemergence barrier plate 23.

In this manner, extra security may be provided against the reemergence of the needle tip 3 from the case 1.

While the present invention has been illustrated by the description of embodiments thereof, and while the embodiments have been described in considerable detail, it is not intended to restrict or in any way limit the scope of the appended claims to such detail. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope or spirit of the general inventive concept.

What is claimed is:

1. A protective device for a needle having a needle tip and a needle shaft, said device comprising:

a containment case having a cavity therein through which a needle is received;

a canting plate within said cavity, said plate having a hole through which the needle is received, said hole having an inner face surface bounded by first and second circumferential edges that provide a close sliding fit around the needle;

a sensing arm coupled to the canting plate to align the circumferential edges for sliding engagement with the needle while the needle tip protrudes from the containment case;

resilient biasing means acting between the case and the sensing arm and canting plate to cause the canting plate and the sensing arm to rotate with respect to the needle upon withdrawal of the needle tip into the containment cavity;

a sensing limb on the sensing arm that contacts the shaft of the needle before the needle is withdrawn into the containment cavity, restraining the sensing arm and canting plate from rotating so long as the sensing limb remains in contact with the shaft of the needle, but permitting such rotation, once the sensing limb ceases to be in contact with the shaft of the needle;

a first pressure point present on the canting plate and a first abutment means present and carried within the cavity of the containment case in alignment for contact therebetween;

a second pressure point present on the sensing arm and rotatable therewith and a second abutment means carried within the cavity of the containment case, the second abutment means defining a surface extending generally transversely between and spaced away from opposed apertures of the containment case through which the needle shaft extends, the second pressure point and the second abutment means being out of alignment for contact therebetween with the sensing arm in a first position restrained from rotation and being aligned for contact therebetween with the sensing arm in a second position after rotating;

the first pressure point being positioned to engage with the first abutment means upon withdrawal of the needle tip into the needle guard cavity, such engagement effecting the canting of the canting plate, and the second pressure point being positioned to engage with the second abutment means once the canting plate has assumed a canted orientation but not to engage with the second abutment means before the canting plate has assumed a canted orientation whereby, upon any attempt to further retract the needle from the needle guard, the canting of the canting plate causes the first and second circumferential edges bounding the hole in the canting plate to be directed into locking engagement with the surface of the needle shaft, and, upon any attempt to cause reemergence of the needle tip from the needle guard, contact between the second pressure point and second abutment means tends to rotate the canting plate so as to further engage the circumferential edges with the surface of the needle shaft, to thereby lockingly contain the needle tip within the containment case of the needle guard against either further withdrawal of the needle or reemergence of the needle tip.

2. The protective device of claim 1 wherein the sensing arm comprises a limb that bears against the needle shaft while the needle tip protrudes from the containment casing preventing the canting plate from rotating with respect to the needle so long as the limb on the sensing arm bears against the needle shaft, which limb, upon retraction of the needle tip past this limb, becomes free to rotate, allowing the canting plate to take up a canting orientation that permits locking engagement of the needle guard with the needle.

3. The protective device of claim 2 wherein the limb on the sensing arm comprises a plate with a hole positioned and dimensioned to receive the needle therethrough before the needle is withdrawn into the needle guard.

4. The protective device of claim 2 wherein the limb on the sensing arm comprises a plate with a slot positioned and dimensioned to receive the needle therethrough before the needle is withdrawn into the needle guard.

5. The protective device of claim 2 wherein the limb on the sensing arm comprises a finger that prevents displacement of the limb and sensing arm so long as the finger bears against the needle shaft.

6. The protective device of claim 1, the canting plate being shiftable with respect to the containment case in both longitudinal directions of the needle.

7. The protective device of claim 1 further comprising a resilient member positioned to bias the canting plate at one end for displacement towards the needle tip.

8. A protective device for a needle having a needle tip and a needle shaft, said device comprising:
- a containment case having a cavity through which a needle is received;
- a canting plate within said cavity, said plate having a hole through which the needle is received, said hole having an inner face surface bounded by first and second circumferential edges that provide a close sliding fit around the needle, the canting plate being shiftable with respect to the containment case in both longitudinal directions of the needle;
- a sensing arm coupled to the canting plate to align the circumferential edges for sliding engagement with the needle while the needle tip protrudes from the containment case;
- resilient biasing means acting between the case and the sensing arm and canting plate to cause the canting plate and the sensing arm to rotate with respect to the needle upon withdrawal of the needle tip into the containment cavity;
- a sensing limb on the sensing arm that contacts the shaft of the needle before the needle is withdrawn into the containment cavity, restraining the sensing arm and canting plate from rotating so long as the sensing limb remains in contact with the shaft of the needle, but permitting such rotation, once the sensing limb ceases to be in contact with the shaft of the needle;
- a first pressure point present on the canting plate and a first abutment means present and carried within the cavity of the containment case in alignment for contact therebetween;
- a second pressure point present on the sensing arm and rotatable therewith and a second abutment means carried within the cavity of the containment case, the second abutment means defining a surface extending generally transversely between and spaced away from opposed apertures of the containment case through which the needle shaft extends, the second pressure point and the second abutment means being out of alignment for contact therebetween with the sensing arm in a first position restrained from rotation and being aligned for contact therebetween with the sensing arm in a second position after rotating;
- a resilient member positioned to bias the canting plate at one end for displacement towards the needle tip;
- the first pressure point being positioned to engage with the first abutment means upon withdrawal of the needle tip into the needle guard cavity, such engagement effecting the canting of the canting plate, and the second pressure point being positioned to engage with the second abutment means once the canting plate has assumed a canted orientation but not to engage with the second abutment means before the canting plate has assumed a canted orientation whereby,
- upon any attempt to further retract the needle from the needle guard, the canting of the canting plate causes the first and second circumferential edges bounding the hole in the canting plate to be directed into locking engagement with the surface of the needle shaft, and,
- upon any attempt to cause reemergence of the needle tip from the needle guard, contact between the second pressure point and second abutment means tends to rotate the canting plate so as to further engage the circumferential edges with the surface of the needle shaft,
- to thereby lockingly contain the needle tip within the containment case of the needle guard against either further withdrawal of the needle or reemergence of the needle tip.

9. The protective device of claim 8 wherein the sensing arm comprises a limb that bears against the needle shaft while the needle tip protrudes from the containment casing preventing the canting plate from rotating with respect to the needle so long as the limb on the sensing arm bears against the needle shaft, which limb, upon retraction of the needle tip past this limb, becomes free to rotate, allowing the canting plate to take up a canting orientation that permits locking engagement of the needle guard with the needle.

10. The protective device of claim 9 wherein the limb on the sensing arm comprises a plate with a hole positioned and dimensioned to receive the needle therethrough before the needle is withdrawn into the needle guard.

11. The protective device of claim 9 wherein the limb on the sensing arm comprises a plate with a slot positioned and dimensioned to receive the needle therethrough before the needle is withdrawn into the needle guard.

12. The protective device of claim 9 wherein the limb on the sensing arm comprises a finger that prevents displacement of the limb and sensing arm so long as the finger bears against the needle shaft.

13. The protective device of claim 8 wherein the resilient member comprises a pad.

* * * * *